(12) United States Patent
Deng et al.

(10) Patent No.: US 11,198,638 B2
(45) Date of Patent: Dec. 14, 2021

(54) BIOACTIVE BORATE GLASS AND METHODS THEREOF

(71) Applicant: CORNING INCORPORATED, Corning, NY (US)

(72) Inventors: Huayun Deng, Painted Post, NY (US); Qiang Fu, Pianted Post, NY (US); Ying Wei, Pianted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 16/202,873

(22) Filed: Nov. 28, 2018

(65) Prior Publication Data

US 2019/0161392 A1 May 30, 2019

Related U.S. Application Data

(60) Provisional application No. 62/591,429, filed on Nov. 28, 2017.

(51) Int. Cl.
| | |
|---|---|
| *C03C 4/00* | (2006.01) |
| *A61K 8/28* | (2006.01) |
| *C03C 3/21* | (2006.01) |
| *A61K 8/24* | (2006.01) |
| *A61Q 11/00* | (2006.01) |
| *A61P 43/00* | (2006.01) |
| *C03C 3/19* | (2006.01) |
| *C03C 3/247* | (2006.01) |
| *A61K 8/21* | (2006.01) |
| *A61K 33/42* | (2006.01) |
| *A61K 33/08* | (2006.01) |
| *A61K 33/22* | (2006.01) |
| *A61K 6/20* | (2020.01) |
| *A61K 6/818* | (2020.01) |
| *A61K 6/833* | (2020.01) |
| *A61K 6/836* | (2020.01) |

(52) U.S. Cl.
CPC .............. *C03C 4/0021* (2013.01); *A61K 6/20* (2020.01); *A61K 6/818* (2020.01); *A61K 6/833* (2020.01); *A61K 6/836* (2020.01); *A61K 8/21* (2013.01); *A61K 8/24* (2013.01); *A61K 8/28* (2013.01); *A61K 33/08* (2013.01); *A61K 33/22* (2013.01); *A61K 33/42* (2013.01); *A61P 43/00* (2018.01); *A61Q 11/00* (2013.01); *C03C 3/19* (2013.01); *C03C 3/21* (2013.01); *C03C 3/247* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 2,532,386 | A | 12/1950 | Armistead |
| 2,978,339 | A | 4/1961 | Franklin et al. |
| 2,987,339 | A | 4/1961 | Veatch et al. |
| 3,323,888 | A | 6/1967 | Searight et al. |
| 3,778,335 | A | 12/1973 | Boyd |
| 3,790,430 | A | 2/1974 | Mochel |
| 4,083,727 | A | 4/1978 | Andrus et al. |
| 4,084,972 | A | 4/1978 | Andrus et al. |
| 4,126,437 | A | 11/1978 | O'Horo |
| 4,140,645 | A | 2/1979 | Beall et al. |
| 4,233,169 | A | 11/1980 | Beall et al. |
| 4,323,056 | A | 4/1982 | Borrelli et al. |
| 4,340,693 | A | 7/1982 | Drake et al. |
| 4,391,646 | A | 7/1983 | Howell |
| 4,889,707 | A | 12/1989 | Day et al. |
| 5,081,394 | A | 1/1992 | Morishita et al. |
| 5,153,070 | A | 10/1992 | Andrus et al. |
| 5,217,928 | A | 6/1993 | Goetz et al. |
| 5,648,124 | A | 7/1997 | Sutor |
| 5,674,790 | A | 10/1997 | Araujo |
| 5,849,816 | A | 12/1998 | Suskind et al. |
| 5,876,452 | A | 3/1999 | Athanasiou et al. |
| 6,034,014 | A | 3/2000 | Rapp et al. |
| 6,214,471 | B1 | 4/2001 | Beall et al. |
| 6,254,981 | B1 | 7/2001 | Castle |
| 6,280,863 | B1 | 8/2001 | Frank et al. |
| 6,328,990 | B1 | 12/2001 | Ducheyne et al. |
| 6,338,751 | B1 | 1/2002 | Litkowski et al. |
| 6,506,399 | B2 | 1/2003 | Donovan |
| 6,514,892 | B1 | 2/2003 | Kasai et al. |

(Continued)

FOREIGN PATENT DOCUMENTS

| | | |
|---|---|---|
| CA | 2577628 C | 3/2006 |
| CA | 2926665 A1 | 5/2015 |

(Continued)

OTHER PUBLICATIONS

Harianawala et al (J Adv Med Dent Sci Res, 2016, 4(3), 35-39) (Year: 2016).*
Ohgushi et al; Bioceramics vol. 11, LeGeros et al, Ed., Proc. 11th Int. Symp. Ceramics Med. (NY:NY), Nov. 1998, pp. 261-264 (Year: 1998).
Peddi et al; "Bioactive Borate Glass Coatings for Titanium Alloys", J. Mater. Sci: Mater. Med., (2008), 19, p. 3145-3152.
Rahaman et al; "Bioactive Glass in Tissue Engineering", Acta Biomaterialia, 7, (2011), 2355-2373.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.

(Continued)

*Primary Examiner* — Celeste A Roney
(74) *Attorney, Agent, or Firm* — Shantanu C. Pathak

(57) ABSTRACT

A bioactive borate glass composition including, for example: 30 to 60% $B_2O_3$; 0.5 to 20% $ZrO_2$; 3 to 30% $Na_2O$; 0.1 to 15% $K_2O$; 0.1 to 15% MgO; 5 to 30% CaO; and 1 to 5% $P_2O_5$ in mole percents based on 100 mol % of the total composition. Also disclosed is a method of making and method of using the compositions and the bioactive borate glass dentin treatment formulations.

6 Claims, 4 Drawing Sheets

(56) References Cited

U.S. PATENT DOCUMENTS

| | | | |
|---|---|---|---|
| 6,802,894 B2 | 10/2004 | Brodkin et al. | |
| 6,838,171 B2 | 1/2005 | Normura | |
| 6,852,656 B1 | 2/2005 | La Greca et al. | |
| 7,047,634 B2 | 5/2006 | Nakamura | |
| 7,047,637 B2 | 5/2006 | DeRochemont et al. | |
| 7,166,548 B2 | 1/2007 | Apel et al. | |
| 7,166,549 B2 | 1/2007 | Fechner et al. | |
| 7,192,602 B2 | 3/2007 | Fechner et al. | |
| 7,316,740 B2 | 1/2008 | Schweiger et al. | |
| 7,597,900 B2 | 10/2009 | Zimmer et al. | |
| 7,704,903 B2 | 4/2010 | Seneschal et al. | |
| 7,709,027 B2 | 5/2010 | Fechner et al. | |
| 7,905,115 B2 | 3/2011 | Rake et al. | |
| 7,989,065 B2 | 8/2011 | Winstead et al. | |
| 8,080,490 B2 | 12/2011 | Fechner et al. | |
| 8,173,154 B2 | 5/2012 | Jung et al. | |
| 8,637,300 B2 | 1/2014 | Ruf et al. | |
| 9,056,045 B2 | 6/2015 | Hughes | |
| 9,084,844 B2 | 7/2015 | Vallittu | |
| 9,101,439 B2 | 8/2015 | Ritzberger et al. | |
| 9,168,272 B2 | 10/2015 | Hill et al. | |
| 9,232,989 B2 | 1/2016 | Ritzberger et al. | |
| 9,238,044 B2* | 1/2016 | Da Fonte Ferreira | A61L 27/10 |
| 9,241,879 B2 | 1/2016 | Castillo | |
| 9,326,995 B2 | 5/2016 | Stucky et al. | |
| 9,498,459 B2 | 11/2016 | Pomrink et al. | |
| 9,622,483 B2 | 4/2017 | Bookbinder et al. | |
| 9,688,567 B2 | 6/2017 | Rampf et al. | |
| 9,701,573 B2 | 7/2017 | Beall et al. | |
| 2004/0120908 A1 | 6/2004 | Cohen et al. | |
| 2004/0166172 A1 | 8/2004 | Rosati et al. | |
| 2004/0228905 A1 | 11/2004 | Greenspan et al. | |
| 2005/0118236 A1 | 6/2005 | Qiu et al. | |
| 2005/0142077 A1 | 6/2005 | Zimmer et al. | |
| 2005/0158395 A1 | 7/2005 | Zimmermann et al. | |
| 2006/0127427 A1 | 6/2006 | Vernice et al. | |
| 2006/0292280 A1 | 12/2006 | Soper et al. | |
| 2007/0122356 A1 | 5/2007 | Kessler et al. | |
| 2008/0214428 A1 | 9/2008 | Orlich et al. | |
| 2008/0233201 A1 | 9/2008 | Royere et al. | |
| 2009/0208428 A1 | 8/2009 | Hill et al. | |
| 2009/0324668 A1 | 12/2009 | Kangasniemi et al. | |
| 2011/0008293 A1 | 1/2011 | Bhandari | |
| 2011/0009254 A1 | 1/2011 | Schweiger et al. | |
| 2011/0152057 A1 | 6/2011 | Qi | |
| 2012/0020898 A1 | 1/2012 | Mandadi et al. | |
| 2012/0135848 A1 | 5/2012 | Beall et al. | |
| 2012/0317735 A1 | 12/2012 | Gonzales et al. | |
| 2012/0321567 A1 | 12/2012 | Gonzales et al. | |
| 2013/0011446 A1 | 1/2013 | Depaula | |
| 2013/0266625 A1 | 10/2013 | Benita et al. | |
| 2014/0000891 A1 | 1/2014 | Mahoney et al. | |
| 2014/0026916 A1 | 1/2014 | Havens et al. | |
| 2014/0186274 A1 | 7/2014 | Hodgkinson | |
| 2014/0193499 A1 | 7/2014 | Da Fonte Ferreira et al. | |
| 2014/0212469 A1 | 7/2014 | Rahaman et al. | |
| 2014/0219941 A1 | 8/2014 | Takekawa et al. | |
| 2014/0271913 A1 | 9/2014 | Pomrink et al. | |
| 2014/0349831 A1 | 11/2014 | Cornejo et al. | |
| 2014/0370464 A1 | 12/2014 | Kounga et al. | |
| 2015/0087493 A1 | 3/2015 | Ritzberger et al. | |
| 2015/0104655 A1 | 4/2015 | Kim et al. | |
| 2015/0231042 A1 | 8/2015 | Gonzales et al. | |
| 2015/0239772 A1 | 8/2015 | Baker et al. | |
| 2015/0265509 A1 | 9/2015 | Zhang et al. | |
| 2015/0274581 A1 | 10/2015 | Beall et al. | |
| 2015/0299031 A1 | 10/2015 | Ritzberger et al. | |
| 2015/0374589 A1 | 12/2015 | Rempf et al. | |
| 2016/0060159 A1 | 3/2016 | Kim et al. | |
| 2016/0102010 A1 | 4/2016 | Beall et al. | |
| 2016/0145567 A1 | 5/2016 | Henry et al. | |
| 2016/0340239 A1 | 11/2016 | Propster et al. | |
| 2017/0086877 A1 | 3/2017 | Moffarah et al. | |
| 2017/0274118 A1 | 9/2017 | Nazhat et al. | |
| 2017/0340527 A1 | 11/2017 | Chang et al. | |
| 2017/0340666 A1 | 11/2017 | Deng et al. | |
| 2017/0341975 A1 | 11/2017 | Gross et al. | |
| 2017/0342382 A1 | 11/2017 | Deng et al. | |
| 2017/0342383 A1 | 11/2017 | Deng et al. | |
| 2017/0349876 A1* | 12/2017 | Deng | C03C 3/064 |
| 2017/0354755 A1 | 12/2017 | Weinberger et al. | |
| 2018/0343255 A1 | 11/2018 | Thibadeau, Sr. et al. | |
| 2019/0048318 A1 | 2/2019 | Deng et al. | |
| 2019/0060523 A1* | 2/2019 | Bakry | A61L 27/54 |

FOREIGN PATENT DOCUMENTS

| | | |
|---|---|---|
| CN | 1325291 A | 12/2001 |
| CN | 1838936 A | 9/2006 |
| CN | 101018573 A | 8/2007 |
| CN | 101596326 A | 12/2009 |
| CN | 101704632 A | 5/2010 |
| CN | 102421716 A | 4/2012 |
| CN | 102526797 A | 7/2012 |
| CN | 103172263 A | 6/2013 |
| CN | 103930086 A | 7/2014 |
| CN | 103979796 A | 8/2014 |
| CN | 104039729 A | 9/2014 |
| CN | 104108883 A | 10/2014 |
| CN | 104379113 A | 2/2015 |
| CN | 104736126 A | 6/2015 |
| EP | 0583791 A1 | 2/1994 |
| EP | 1123072 A1 | 8/2001 |
| EP | 1452496 A1 | 9/2004 |
| EP | 1021148 B1 | 5/2008 |
| HU | 227595 B1 | 9/2011 |
| JP | 2004359754 A | 12/2004 |
| JP | 2005-053776 A | 3/2005 |
| JP | 2007001846 A | 1/2007 |
| JP | 2007039269 A | 2/2007 |
| JP | 2015-504399 A | 2/2015 |
| JP | 2015-505786 A | 2/2015 |
| JP | 2015-509016 A | 3/2015 |
| JP | 2015-525180 A | 9/2015 |
| KR | 2007081952 A | 8/2007 |
| KR | 10-0781952 B1 | 12/2007 |
| KR | 10-2013-0112422 A | 10/2013 |
| KR | 20130112433 A | 10/2013 |
| WO | 1991012032 A1 | 8/1991 |
| WO | 1997018171 A1 | 5/1997 |
| WO | 9727148 A1 | 7/1997 |
| WO | 9815263 A2 | 4/1998 |
| WO | 1999062835 A1 | 12/1999 |
| WO | 00/15167 A1 | 3/2000 |
| WO | 01/34060 A1 | 5/2001 |
| WO | 2007/022264 A2 | 2/2007 |
| WO | 2007141978 A1 | 12/2007 |
| WO | 2008000888 A2 | 1/2008 |
| WO | 2011/084572 A2 | 7/2011 |
| WO | 2011141896 A1 | 11/2011 |
| WO | 2014/015240 A1 | 1/2014 |
| WO | 2014095198 A1 | 6/2014 |
| WO | 2015034860 A1 | 3/2015 |
| WO | 2015123049 A1 | 8/2015 |
| WO | 2015200017 A1 | 12/2015 |

OTHER PUBLICATIONS

Raszewski et al; "Methods for Producing Hollow Glass Microspheres"; Savannah River National Laboratory, Aiken SC 29808, Mar. 2016.
Rochman et al; "Scientific Evidence Supports a Ban on Microbeads", Environ Sci & Tech, 2015, 49: 10759-10761.
Saranti, et al., "Bioactive Glasses in the System CaO—B2O3—P2O5: Preparation, Structural Study and In Vitro Evaluation." Journal of Non-Crystalline Solids 352, No. 5 (2006): 390-398.
Sglavo; "Chemical Strengthening of Soda Lime Silicate Float Glass: Effect of Small Differences in the KNO3 Bath," Int J Appl Glass Sci, 2015, 6: 72-82.
Simhan; "Chemical Durability of ZrO2 Containing Glasses"; Journal of Non-Crystalline Solids; 54 (1983) 335-343.
Singh et al; "Characterization of SiO2—Na2O≤Fe2O3—CaO—P2O5_B2O3 Glass Ceramics"; Journal of Materials Science: Materials in Medicine, 10(8) pp. 481-484. (1999).

(56) References Cited

OTHER PUBLICATIONS

Strassler et al; "Dentinal Hypersensitivity: Etiology, Diagnosis and Management"; 9 Pages; Date Unknown; www.indeedce.com.
Succaria et al; "Prescribing a Dental Ceramic Material: Zirconia vs Lithium-Disilicate"; The Saudi Dent J, 2011, 23: 165-166.
Tilocca et al., "Structural Effects of Phosphorus Inclusion in Bioactive Silicate Glasses", J. Phys. Chem. B 2007, 111, 14256-14264.
Topuz, et al., "Magnesium Ions and Alginate Do Form Hydrogels: A Rheological Study"; Soft Matter, 2012, 8, 4877-4881.
Uo et al; "Properties and Cytotoxicity of Water Soluble Na2O—CaO—P2O5 Glasses"; Biomaterials, 19, (1998), 2277-2284.
Wallenberger et al; "The Liquidus Temperature; Its Critical Role in Glass Manufacturing"; International Journal of Applied Glass Science 1 [2] (2010) pp. 151-163.
Xiao et al; "Hollow Hydroxyapatite Microspheres: A Novel Bioactive and Osteoconductive Carrier for Controlled Release of Bone Morphogenetic Protein-2 in Bone Regeneration", Acta Biomater. Sep. 2013; 9(9): 8374-8383.
Yao et al; "In Vitro Bioactive Characteristics of Borate-Based Glasses With Controllable Degradation Behavior"; J. Am. Ceram. Soc.; 90 [1]; 303-306 (2007).
Yin et al; "Effect of ZrO2 on the Bioactivity Properties of Gel-Derived CaO—P2O5—SiO2—SrO Glasses"; Ceramics International; 43 (2017) pp. 9691-9698.
Yuan et al; "Osteoinduction by Calciumphosphate Biomaterials", Journal of Materials Science: Materials in Medicine 9 (1998) 723-726.
Yue et al; "Fiber Spinnability of Glass Melts"; International Journal of Applied Glass Science; (2016) pp. 1-11.
Zanotto, "A Bright Future for Glass-Ceramics", American Ceramic Society Bulletin, vol. 89, No. 8, pp. 19-27, 2010.
Zhang et al; "Chipping Resistance of Graded Zirconia Ceramics for Dental Crowns"; J Dent Res, 2012, 91:311-315.
Mohini et al; "Studies on Influence of Aluminium Ions on the Bioactivity of B2O3—SiO2—P2O5—Na2O—CaO Glass System by Means of Spectroscopic Studies" ; Applied Surface Science; 287 (2013) pp. 46-53.
Noris-Suarez et al; "Osteoblastic Cells Biomineralized on Bioactive Glass and Glass-Ceramics of the SiO2Na20.CaO.K2O.MgO.P2O5 System Modified With Al2O3 and B2O3"; Journal of Ceramic Processing Research; vol. 11, No. 2 (2010) pp. 129-137.
Fires et al; "The Role of Alumina in Aluminoborosilicate Glasses for Use in Glass-Ionomer Cements" ; J. Mater. Chem, 19 (2009) pp. 3652-3660.
Ahmed et al; "Processing, Characterisation and Biocompatibility of Iron-Phosphate Glass Fibres for Tissue Engineering", Biomaterials, 25, (2004), 3223-3232.
American Type Culture Collection, Product Sheet MC3T3E1, Subclone 14, (ATCC® CRL2594™), p. 1-3, Aug. 2014.
Apel et al., "Influence of ZrO2 on the Crystallization and Properties of Lithium Disilicate Glass-Ceramics Derived From a Multi-Component System", J Eur Ceram Soc, 2007, 27:1571-1577.
Bertling, et al., "Hollow Microspheres". Chem Eng Technol, 2004, 27: 829-837.
Brown et al; "Effect of Borate Glass Composition on Its Conversion to Hydroxyapatite and on the Proliferation of MC3T3-E1 Cells"; Journal of Biomedical Materials Research Part A 88, No. 2, (2009): 392-400.
Budov, "Hollow Glass Microspheres. Use, Properties and Technology (Review Article)", Glass Ceram, 1994, 51: 230-235.
Bunker, et al., "Phosphate Glass Dissolution in Aqueous Solutions", Journal of Non-Crystalline Solids 64 (1984) 291-316.
Cao et al; "Bioactive Materials"; Ceramics International, 22, (1996) 493-507.
Cao et al; "Methods for Biomimetic Remineralization of Human Dentine: A Systematic Review"; Int. J. Mol. Sci. (2015) 16; pp. 4615-4627.
Copeland et al; "Microbeads: An Emerging Water Quality Issue", Retrieved From fas.org, Jul. 20, 2015, 2 Pgs.
Coradin et al; "Silica-Alginate Composites for Microencapsulation" Applied Microbiology and Biotechnology, 61(5-6) pp. 429-434 (2003).
Davari, "Dentin Hypersensitivity: Etiology, Diagnosis and Treatment, A Literature Review," J Dent (Shiraz), 2013, 14(3): 136-145).
De Kerchove et al., "Formation of Polysaccharide Gel Layers in the Presence of Ca2+ and K+ Ions: Measurements and Mechanisms", Biomacromolecules 2007, 8, 113-121.
El-Kheshen et al; "Effect of Al2O3 Addition on Bioactivity, Thermal and Mechanical Properties of Some Bioactive Glasses"; Ceramics Int. (2008) 34: 1667-1673 (Year: 2008).
Fendall et al; "Contributing to Marine Pollution by Washing Your Face: Microplasitcs in Facial Cleansers"; Marine Pollution Bulletin 58 (8): 1225-1228 (2009)).
Forsback et al; "Mineralization of Dentin Induced by Treatment With Bioactive Glass S53P4 In Vitro"; Acta Odontol Scand, 62 (2004); pp. 14-20.
Franks et al; "The Effect of MgO on the Solubility Behaviour and Cell Proliferation in a Quaternary Soluble Phosphate Based Glass System", J. of Mate. Science: Materials in Medicine, 13, (2002), 549-556.
Fu et al; "Bioactive Glass Innovations Through Academia-Industry Collaboration"; International Journal of Applied Glass Science, 7 [2], (2016) pp. 139-146.
Fu et al; "Bioactive Glass Scaffolds for Bone Tissue Engineering: State of the Art and Future Perspectives", Materials Science and Engineering, C 31, (2011), 1245-1256.
Fu et al; "Hollow Hydroxyapatite Microspheres as a Device for Controlled Delivery of Proteins"; J Mater Sci: Mater Med., 2011;22:579-91.
Fu et al; "Nature-Inspired Design of Strong, Tough Glass-Ceramics," MRS Bulletin, 2017, 42:220-225.
Fu et al; "Silicate, Borosilicate, and Borate Bioactive Glass Scaffolds With Controllable Degradation Rate for Bone Tissue Engineering Application. I. Preparation and In Vitro Degradation"; J. Biomed. Res. (2010) 95A(1): 164-171(Year:2010).
Graham, "High-Sensitivity Manetization Measurements", J. Mater. Sci. Technol., vol. 16, No. 2, 2000, p. 97-101.
Gy, "Ion Exchange for Glass Strengthening," Mater Sci EHG B 2008, 149: 159-165.
Han et al; "In Vivo Remineralization of Dentin Using an Agarose Hydrogel Biomimetic Mineralization System"; Nature, Scientific Reports; (2017); 9 Pages.
Hench et al; "Third-Generation Biomedical Materials", Science, vol. 295, Feb. 8, 2002, p. 1016-1017, www.sciencemag.org, Downloaded From www.sciencemag.org on Aug. 5, 2015.
Hench; "Bioceramics", J. Am. Ceram. Soc., 81, (7), 1705-1728 (1998).
Hiorth et al; "Immersion Coating of Pellets With Calcium Pectinate and Chitosan"; International Journal of Pharmaceutics 308 (2006) 25-32.
Holand et al; "A Comparison of the Microstructure and Properties of the IPS EMPRESST2 and the IPS EMPRESST Glass-Ceramics"; J Biomed Mater Res (Appl Biomater), 2000, 53: 297-303.
Huang, et al; "Kinetics and Mechanisms of the Conversion of Silicate (45S5), Borate and Borosilicate Glasses to Hydroxyapatite in Dilute Phosphate Solutions," J Mater Sci Mater Med 2006, 17: 583-596.
International Search Report and Written Opinion of the International Searching Authority; PCT/US2018/062673; dated Jan. 25, 2019; 13 Pages; European Patent Office.
Jacoby; "New Applications for Glass Emerge," Chem. Eng. News, 90 [25] 34-36 (2012).
Jones; "Review of Bioactive Glass: From Hench to Hybrids"; Acta Biomaterialia 9 (2013) pp. 4457-4486.
Knowles; "Phosphate Based Glasses for Biomedical Applications"; J. Mater. Chem. 2003, 13, 2395-2401.
Kokubo et al; "How Useful is SBF in Predicting In Vivo Bone Bioactivity?"; Biomaterials, 27, (2006), 2907-2915.
Kulal et al; "An In-Vitro Comparison of Nano Hydroxyapatite, Novamin and Proargin Desensitizing Toothpastes—A Sem Study"; Journal of Clinical and Diagnostic Research; 2016; vol. 10 (10) ZC51-ZC54.

(56) References Cited

OTHER PUBLICATIONS

Kumaryadav et al; "Development of Zirconia Substituted 1393 Bioactive Glass for Orthopaedic Application"; Oriental Journal of Chemistry; vol. 33, No. 6; (2017) pp. 2720-2730.

Lien et al; "Microstructural Evolution and Physical Behavior of a Lithium Disilicate Glass-Ceramic"; Dent Mater 2015, 31: 928-940.

Low et al; "Reduction in Dental Hypersensitivity With Nano-Hydroxyapatite, Potassium Nitrate, Sodium Monoflurophosphate and Antioxidants"; The Open Dentistry Journal; (2015), 9, pp. 92-97.

Lu et al; "The Biodegradation Mechanism of Calcium Phosphate Biomaterials in Bone"; Journal of Biomedical Materials Research, Aug. 2002, 63(4): 408-412.

Marcolongo et al; "Surface Reaction Layer Formation in Vitro on a Bioactive Glass Fiber/Polymeric Composite"; J. Biomed Mater. Res.; (1997); 37, pp. 440-448.

Miglani et al; "Dentin Hypersensitivity: Recent Trends in Management"; J. Conserv. Dent. 2010; 13 (4) pp. 218-224.

Mintatoya et al; "Bioactive Glass Cloth That Propmotes New Bone Formation"; Key Eng. Mater.; (2013) 529-530; pp. 266-269.

Montazerian et al; "History and Trends of Bioactive Glass-Ceramics", Journal of Biomedical Materials Research A, 2016, vol. 104A, 1231-1249, 2016 Wiley Periodicals, Inc.

Morch et al; "Effect of $Ca^{2+}$, $Ba^{2+}$, and $Sr^{2+}$ on Alginate Microbeads"; Biomacromolecules 2006, 7, 1471-1480.

Murray; "Issues in Boron Risk Assessment: Pivotal Study, Uncertainty Factors, and ADIs"; The Journal of Trace Elements in Experimental Medicine 9, No. 4 (1996): 231-243.

Napper et al; "Characterisation, Quantity and Sorptive Properites of Microplastics Extracted From Cosmetics"; Marine Pollution Bulletin, vol. 99, Issues 1-2, Oct. 15, 2015, pp. 178-185.

Neel et al; "Effect of Iron on the Surface, Degradation and Ion Release Properties of Phosphate Based Glass Fibres." Acta Biomaterialia 1, No. 5 (2005): 553-563.

Neel, et al; "Characterisation of Antibacterial Copper Releasing Degradable Phosphate Glass Fibres." Biomaterials 26, No. 15 (2005): 2247-2254.

Abo-Naf et al; "In Vitro Bioactivity Evaluation, Mechanical Properties and Microstructural Characterization of $Na_2O$—CaO—$B_2O_3$—$P_2O_5$ Glasses"; Spectrochimica Acta Part A: Molecular and Biomolecular Spectroscopy; 144 (2015) pp. 88-98.

Sharmikn et al; "Effect of Boron Additiona on the Thermal, Degradation, and Cytocompatibility Properties of Phosphate-Based Glasses"; Biomed Research Internaitonal; vol. 2013; Article ID 902427; 12 Pages.

Buchilin et al; "Crystallization-Controlled Pore Retention in Calcium-Phosphate Glassceramics From Powder Sintering of CaO—$P_2O_5$—$B_2O_3$—$Al_2O_3$—$TiO_2$—$ZrO_2$ Glass"; Journal of Non-Crystalline Solids; 373-374 (2013) pp. 42-50.

Zheng et al; "Characteristics and Biocompatibility of $Na_2O$—$K_2O$—CaO—MgO—SrO—$B_2O_3$—$P_2O_5$ Borophosphate Glass Fibers"; Journal of Non-Crystalline Solids; 358 (2012) 387-391.

"Azo Materials, ""Silicon Dioxide"", accessed from: ""https://www.azom.com/properties.aspx?ArticleI D=1114"", accessed on Feb. 19, 2019, pp. 1-4 (Year: 2019)".

Kaklamani et al; "Mechanical Properties of Alginate Hydrogels Manufactured Using External Gelation", J. Meech Beh. Biomed, Mater., 2014, pp. 135-142 (Year: 2014).

Maestrelli et al; "Development of Enteric-Coated Calcium Pectinate Microspheres Intended for Colonic Drug Dellvery", Eur. J. Pharm. and Biopharm., 2008, pp. 508-518 (Year: 2008).

Gorustovich et al. "Osteoconductivity of strontium-doped bioactive glass particles: A histomorphometric study in rats," J Biomed Materials Res. Part A (2010) 92A: pp. 232-237.

Andersson et al. "In vivo behaviour of glasses in the $SiO_2$—$Na_2O$—CaO—$P_2O_5$—$Al_2O_3$—$B_2O_3$ system" , J. Mat. Sci: Materials in Medicine (1990) 1: pp. 219-227.

Zahid et al; "Biological Behavior of Bioactive Glasses and Their Composites"; RSC Adv., 2016, 6 pages 70197-70214.

Gunter et al. "Calcium pectinate gel beads obtained from callus cultures pectins aspromising systems for colon-targeted drug delivery," Carbohydrate Polymers, 2016, pp. 490-499.

Ogonczyk et al. "Microfluidic formulation of pectin microbeads for encapsulation and controlled release of nanoparticles," Biomicrofluidics, 2011, pp. 1-12.

Japanese Patent Application No. 2018561573 Office Action dated Feb. 24, 2021, 14 pages (7 pages of English Translation and 7 pages of Original Document); Japanese Patent Office.

Ohgushi et al., "$Al_2O_3$ doped apatite-wollastonite containing glass ceramic provokes osteogenic differentiation of marrow stromal stem cells", J Biomed Mater Re, vol. 44, Issue 4 pp. 381-388.

Zhao et al., "Mechanism for converting $Al_2O_3$-containing borate glass to hydroxyapatite in aqueous phosphate solution", Acta Biomaterialia, Dec. 10, 2008, vol. 5, No. 4, pp. 1265-1273.

Liu et al. "The Effect of Novel Fluorapatite Surfaces on Osteoblast-Like Cell Adhesion, Growth, and Mineralization" Tissue Engineering: Part A, vol. 16, No. 9, 2010 (Year: 2010).

Wang Yingjun, "Biomedical Ceramic Materials", Guangzhou, South China University of Science and Technology Press, , Aug. 31, 2010, pp. 90-93(Original document only).

G. Jagan Mohini et, al., "Studies of aluminum ions on the bioactivity of $B_2O_3$—$SiO_2$—$P_2O_5$—$Na_2O$—CaO glass system by means of spectroscopic", Applied Surface Science, vol. 287, 2013, pp. 46-53.

Karem Noris-Suarez et, al., "Osteoblatsic cells biomineralized on bioactive glass and glass-ceramics of the $SiO_2.Na_2O.CaO.K_2O.MgO.P_2O_5$ system modified with $Al_2O_3$ and $B_2O_3$", Journal of Ceramic Processing Research, vol. 11, No. 2, 2020, 9 pages.

Ricardo A. Pires et, al., "The role of alumina in aluminoborosilicate glasses for use in glass-inomercementa", Journal of Materials Chemistry, vol. 19, 2009, pp. 3652-3660.

\* cited by examiner

BIOACTIVE BORATE GLASS AND METHODS THEREOF

CROSS REFERENCE TO RELATED APPLICATIONS

This application claims the benefit of priority under 35 U.S.C. § 119 of U.S. Provisional Patent Application No. 62/591,429 filed Nov. 28, 2017, the content of which is incorporated herein by reference in its entirety.

The present application is related commonly owned and assigned U.S. Application Nos. 62/342,384, entitled "BIOACTIVE ALUMINOBORATE GLASSES", filed May 27, 2016; and 62/342,411, entitled "BIOACTIVE GLASS MICROSPHERES", filed May 27, 2016, but does not claim priority thereto.

The present application is also related commonly owned and assigned U.S. Application Nos.:

62/591,423 filed Nov. 28, 2017, entitled "BIOACTIVE GLASS COMPOSITIONS AND METHODS OF TREATING DENTIN HYPERSENSITIVITY";

62/591,446 filed Nov. 28, 2017, entitled "HIGH LIQUIDUS VISCOSITY BIOACTIVE GLASS"; and 62/591,438, filed Nov. 28, 2017, entitled "CHEMICALLY STRENGTHENED BIOACTIVE GLASS-CERAMICS", filed concurrently herewith, but does not claim priority thereto.

The entire disclosure of each publication or patent document mentioned herein is incorporated by reference.

BACKGROUND

The disclosure relates to a glass composition, a bioactive glass composition, and to methods of making and using the compositions.

SUMMARY

In embodiments, the disclosure provides bioactive borate glass compositions comprising, for example, 30 to 60% $B_2O_3$, 0.5 to 20% $ZrO_2$, 3 to 30% $Na_2O$, 0.1 to 15% $K_2O$, 0.1 to 15% MgO, 5 to 30% CaO, and 1 to 5% $P_2O_5$ as represented in mole percents based on 100 mol % of the total composition that are, for example, free of $Al_2O_3$, free of $SiO_2$, or free of mixtures thereof.

In embodiments, the disclosure provides bioactive borate glass compositions comprising, for example, 30 to 60% $B_2O_3$, 0.5 to 20% $ZrO_2$, 3 to 30% $Na_2O$, 0.1 to 15% $K_2O$, 5 to 30% CaO, and 1 to 5% $P_2O_5$ in mole percents based on 100 mol % of the total composition that are free of, for example, $Al_2O_3$, $SiO_2$, MgO, or mixtures thereof.

In embodiments, the disclosed bioactive borate glass compositions exhibited excellent biocompatibility.

In embodiments, the disclosure provides a bioactive borate glass composition and formulation that has a plugging rate that is twice as fast compared to, for example, a bioactive 45S5 glass containing formulation in dentin treatment experiments.

In embodiments, the disclosure provides a formulation and method for treating dentin hypersensitivity.

BRIEF DESCRIPTION OF THE DRAWINGS

In embodiments of the disclosure.

DETAILED DESCRIPTION

Figure 1D:
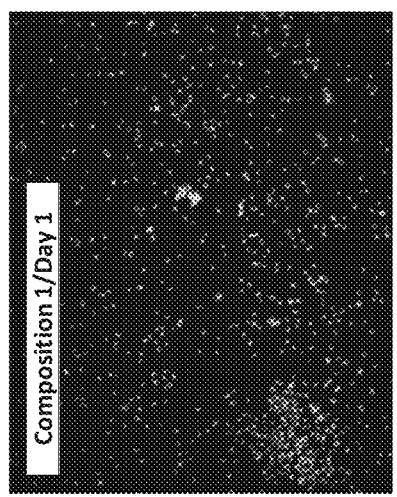
FIGS. 1A to 1F show optical images of cell morphology from live/dead cells assay over a seven (7) day period.
Figure 1E:
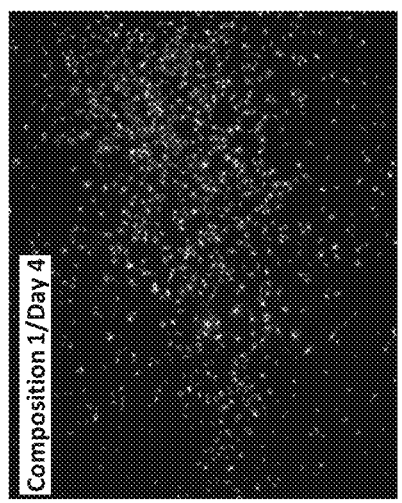
Figure 1A:
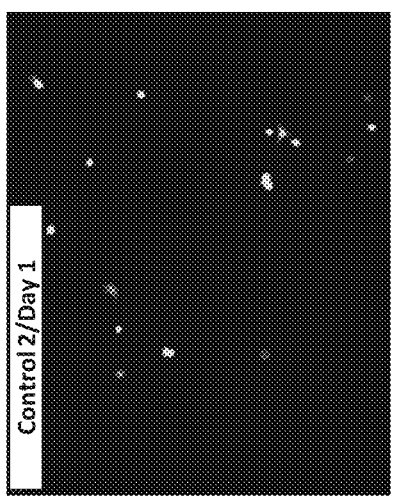
Figure 1B:
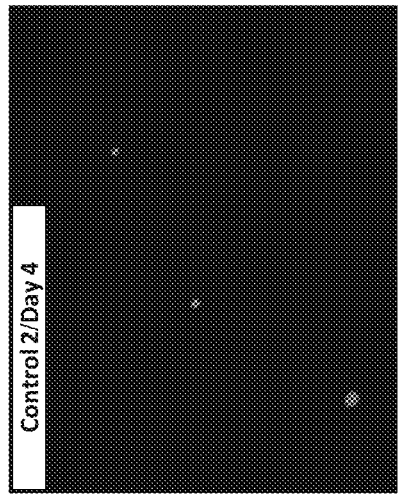
Figure 1F:
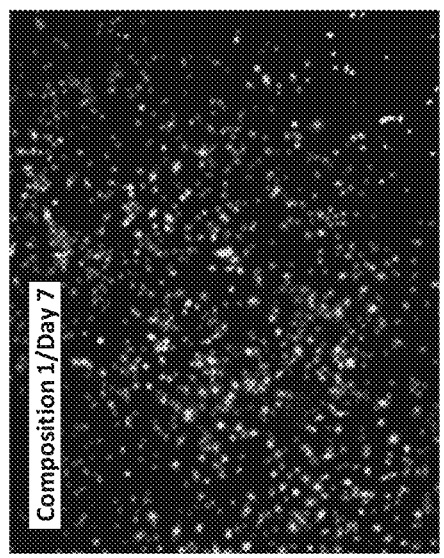
Figure 1C:
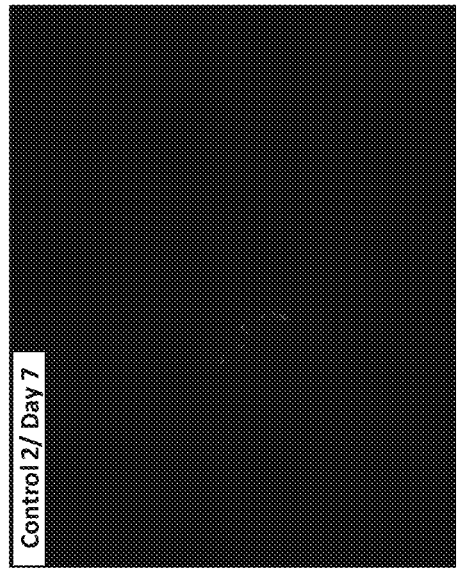

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, and methods of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Dentin hypersensitivity," (DH) "dentin sensitivity," (DS) or like terms refer to a short, sharp pain caused by cold and heat, air, touch, or chemical or osmotic stimuli, e.g., sweets.

"Occlude," "occluding," "occlusion," or like terms refer, for example, to close up or block off, to obstruct.

"Glass," "glasses," or like terms can refer to a glass or a glass-ceramic.

"Glass article," or like terms can refer to any object made wholly or partly of glass or a glass-ceramic.

"Flavorant," "flavor" or like terms can refer to any natural or synthetic substance that provides organoleptic properties to the disclosed composition when a user has contact with the composition. The flavorant can be, for example, a single compound or a mixture of compounds. The flavorant can be selected to give the composition or product a unique flavor or to maintain flavor consistency between different product batches or after recipe changes. The flavorant can be any known or discovered compound, for example, diacetyl, acetylpropionyl, acetoin, isoamyl acetate, benzaldehyde, cinnamaldehyde, ethyl propionate, methyl anthranilate, limonene, ethyl decadienoate, allyl hexanoate, ethyl maltol, ethyl vanillin, methyl salicylate, and like compounds, or mixtures thereof.

Other typical composition components or formulation ingredients are known to one of skill in the art such as an abrasive, a humectant, a colorant, an antibacterial agent, a surfactant, a whitening agent, a binder, and like components or ingredients, see for example, en.wikipedia.org/wiki/Toothpaste.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Bioactive glasses have a widely recognized ability to foster the growth of bone cells, and to bond strongly with hard and soft tissues. Bioactive glasses are also reported to release ions that activate expression of osteogenic genes, and to stimulate angiogenesis (see Rahaman, et al., Bioactive glass in tissue engineering, Acta Biomater, 2011, 7: 2355-2373). Silicate glass based toothpastes such as Novamin® and BioMin® can react with saliva and release calcium, phosphate, or fluoride ions to form hydroxycarbonated apatite or fluorapatite over the exposed dentin and within dentin tubules (see Kulal, "An in-vitro comparison of nano hydroxyapatite, Novamin and Proargin desensitizing toothpastes—a SEM study" J Clin Diagn Res, 2016, 10(10): ZC51-ZC54; U.S. Pat. No. 6,338,751, to L. J. Litkowski, entitled "Compositions containing bioactive glass and their use in treating tooth hypersensitivity"; and U.S. Pat. No. 9,168,272 to Hill entitled "Bioactive glass composition").

Treatment using bioactive glass-containing toothpastes is a method that can provide a long period of dentin protection, for example, several months. Unlike other occluding reagents of dentin tubules, the disclosed bioactive glass formulation can provide long-term treatment.

There has been a growing interest in bioactive borate glasses for their novel properties such as fast degradation and conversion to hydroxyapatite-like materials, supporting angiogenesis, and the regeneration of soft tissue (see Rahaman, et al., supra.). However, the fast release of boron in solution can result in decreased cell viability, especially for in vitro cell cultures. This cell viability problem can be solved by, for example, modifying the glass composition to include some silica, or culturing the cells in a dynamic environment (see Rahaman, et al., supra.). Certain aluminoborate glasses from Corning Incorporated have demonstrated, for example, excellent biocompatability, enhanced angiogenesis, and wound healing promotion (see for example, the abovementioned commonly owned U.S. Ser. Nos. 62/342,384; 62/342,411, and 62/591,423. However, the release of aluminum ion is a potential concern for neuron toxicity in these $Al_2O_3$-containing bioactive glasses. The addition of $ZrO_2$ in silicate glass is known to improve glass durability (see Simhan, "Chemical durability of $ZrO_2$ containing glasses," J Non-Cryst Solids, 1983, 54: 335-343). However, the impact of $ZrO_2$ on the biocompatibility of silicate-free, borate-based glasses is unclear.

In embodiments, the disclosure provides a group of glass compositions based on borate glasses that have excellent biocompatibility. Furthermore, the disclosed glass compositions were capable of plugging dentin tubules, suggesting use in the treatment of dentin hypersensitivity.

In embodiments, the disclosure provides $ZrO_2$-containing borate glass compositions that exhibit excellent biocompatibility and that can be use in treating dentin hypersensitivity.

In embodiments, the glass comprises, as represented by mole percentage, 30 to 60% $B_2O_3$, 0.5 to 20% $ZrO_2$, 3 to 30% $Na_2O$, 0.1 to 15% $K_2O$, 0.1 to 15% MgO, 5 to 30% CaO, and 1 to 5% $P_2O_5$. Example compositions and controls are listed in Table 1. These glasses can typically be melted at a temperature below, for example, 1300° C., in certain embodiments below 1200° C., which makes it possible to melt the compositions in a relatively small commercial glass tank.

Figure 1:
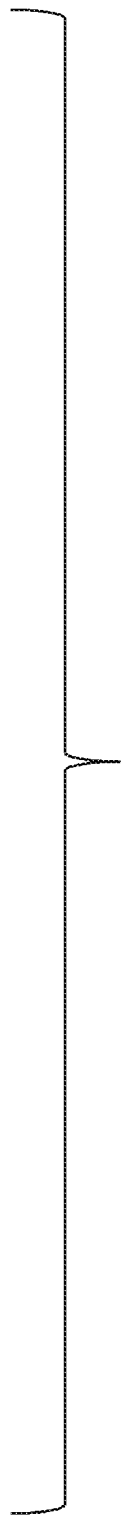
Figure 2:
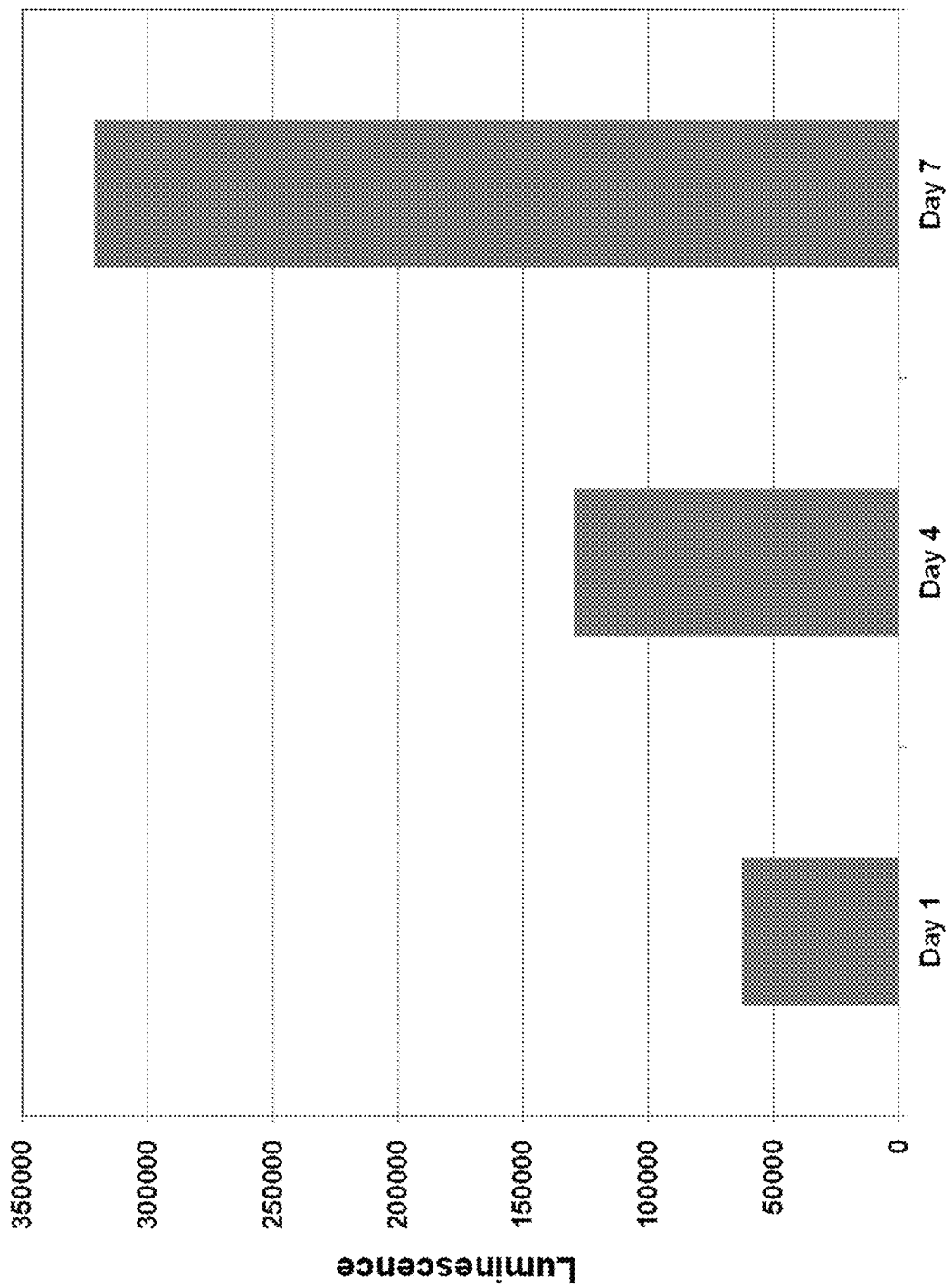
FIG. 2 shows an ATP assay for Example Composition 1.

In embodiments, the addition $ZrO_2$ to borate glasses was unexpectedly found to improve the biocompatibility of the borate glass composition. A substantially higher number of viable cells were seen in the disclosed glass compositions (e.g., disclosed example composition 1), than in a comparative borate glass (e.g., comparative control composition 2) (FIG. 1) that was free of $ZrO_2$ (see Table 1). There were no viable cells on the comparative borate glass disc after 4 days while the cell counts continued to increase in disclosed $ZrO_2$-containing compositions. A continuous cell growth in the disclosed composition was demonstrated using an ATP assay (FIG. 2). The excellent biocompatibility of the disclosed glass compositions is attributed to its lower boron ion release rate, which is believed to be due to the addition or presence of $ZrO_2$ in the composition.

Figure 3:
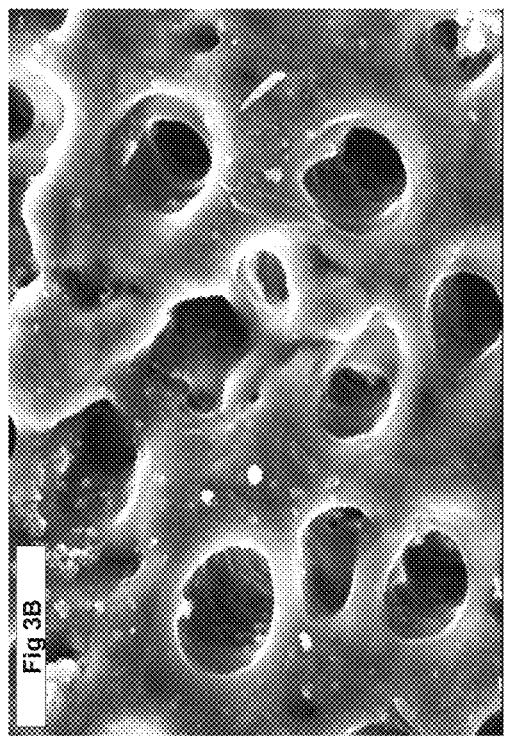
FIGS. 3A to 3D show SEM micrographs of the test dentin discs having different treatments.
Figure 3:
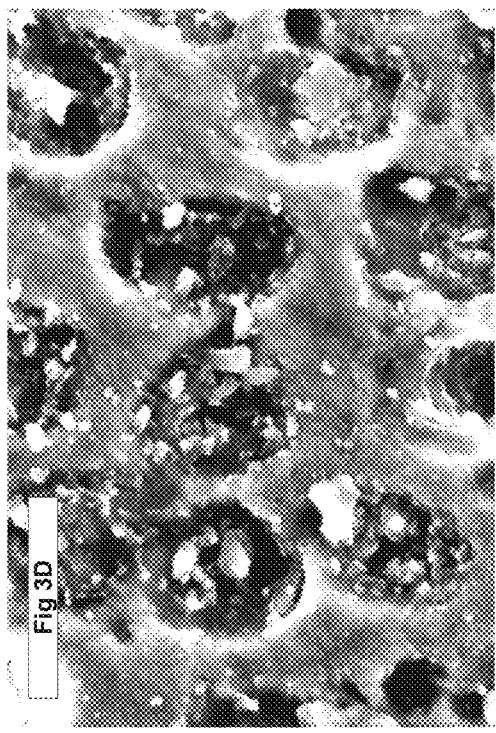
Figure 3:
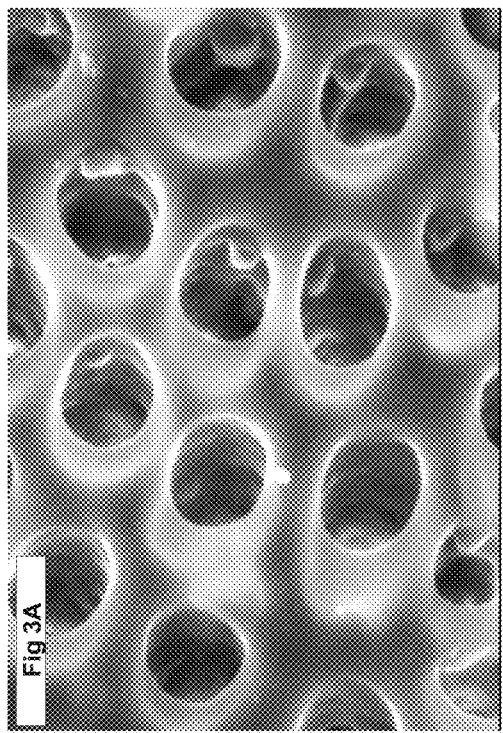
Figure 3:
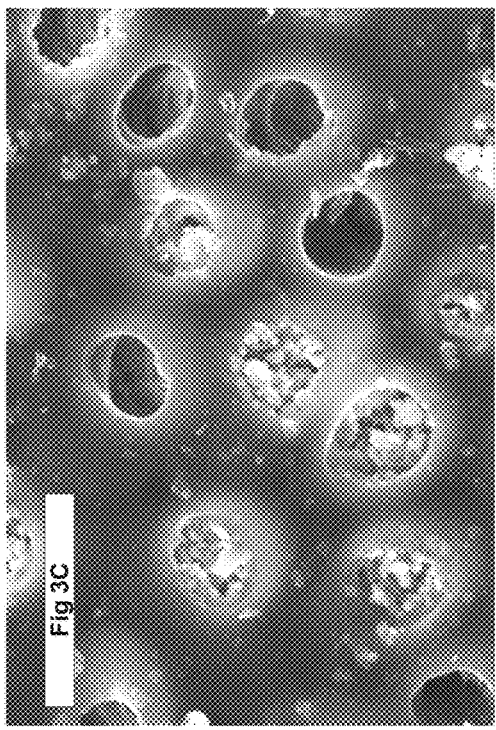

In embodiments, the disclosed compositions can react with saliva and release calcium, phosphate, or fluoride ions to form hydroxycarbonated apatite (FIG. 3) or fluorapatite, exhibiting tubule occlusion at the surface by the formation of a smear layer and within dentin tubules, and rebuild, strengthen, and protect tooth structure. Fluoride ion can be incorporated into the glass compositions in the precursor form as, for example, sodium fluoride (NaF), stannous fluoride ($SnF_2$), calcium fluoride ($CaF_2$), or mixtures thereof, for example, in an amount of from 1 to 25 mol % by super addition to the composition.

In actual oral fluid the fluoride incorporated glasses are expected to release fluoride and form fluorapatite, which is even more resistant to acid dissolution than hydroxycarbonated apatite (HCA).

In embodiments, the disclosed glasses can be processed by various known techniques into, for example, a powder, short fibers, beads, sheets, 3-D scaffolds, and like form factors. A glass powder can generally be prepared by, for example, jet milling or ball milling of glass frits. Short fibers can be made by melt spinning or electric spinning. Beads can be made, for example, by flowing glass particles through a vertical furnace. Sheets can be made, for example, by using thin rolling, float, or fusion-draw processes. Scaffolds can be made using, for example, rapid prototyping, polymer foam replication and particle sintering, and like methods. Glasses of desired forms can be used to, for example, support cell growth, soft and hard tissue regeneration, and stimulation of gene expression or angiogenesis.

The biocompatibility and degradation of the glasses are influenced by the respective glass composition. In the disclosed glass compositions, $B_2O_3$ serves as the primary glass-forming oxide. Borate glass is much less durable than silicate glass, making it attractive for fast degradation. However, the toxicity caused by the degradation and the control of the degradation rate remain a challenge.

$P_2O_5$ also serves as a network former. Furthermore, the liberation of phosphate ions to the surface of bioactive glasses can contribute to the formation of apatite. The provision of phosphate ions by the bioactive glass increases the apatite formation rate and the binding capacity of the bone tissue. In addition, $P_2O_5$ increases the viscosity of the glass, which in turn expands the range of operating temperatures, and is therefore an advantage in the manufacture and the formation of the glass.

In addition to its role as a network former or intermediate in the precursor glasses, $ZrO_2$ improves the chemical durability in the borate glass while having no toxicity concerns.

Alkali oxides (i.e., $Li_2O$, $Na_2O$, $K_2O$, $Rb_2O$, and $Cs_2O$) serve as aids in achieving a low melting temperature and a low liquidus temperature. The addition of alkali oxides has been reported to improve bioactivity (see Rahaman, et al., supra.).

Divalent cation oxides such as alkaline earth oxides can also improve the melting behavior and the bioactivity of the glass. In particular, CaO was discovered to react with $P_2O_5$ to form apatite when immersed in a simulated body fluid (SBF) or in vivo. The release of $Ca^{2+}$ ions from the surface of the glass contributes to the formation of a layer rich in calcium phosphate.

In embodiments, the disclosure provides a bioactive borate glass composition comprising:
30 to 60% $B_2O_3$;
0.5 to 20% $ZrO_2$;
3 to 30% $Na_2O$;
0.1 to 15% $K_2O$;
0.1 to 15% MgO;
5 to 30% CaO; and
1 to 5% $P_2O_5$ in mole percents based on 100 mol % of the total composition.

The mol % of the source has the equivalent weight percentages of: 30 to 60% $B_2O_3$; 0.5 to 20% $ZrO_2$; 3 to 30% $Na_2O$; 0.1 to 15% MgO; 0.1 to 15% MgO; 5 to 30% CaO; and 1 to 5% $P_2O_5$ in weight percents based on 100 wt % of the total composition.

In embodiments, the abovementioned bioactive borate glass composition is free of $Al_2O_3$, free of $SiO_2$, or free of mixtures thereof.

In embodiments, the abovementioned bioactive borate glass composition can further comprise, for example, a source of fluoride ion selected from, for example, sodium fluoride (NaF), stannous fluoride ($SnF_2$), calcium fluoride ($CaF_2$), and like fluoride ion sources, or mixtures thereof.

In embodiments, the disclosure provides a bioactive borate glass composition comprising:
30 to 60% $B_2O_3$;
0.5 to 20% $ZrO_2$;
3 to 30% $Na_2O$;
0.1 to 15% $K_2O$;
5 to 30% CaO; and
1 to 5% $P_2O_5$ in mole percents based on 100 mol % of the total composition.

The mol % of the source has the equivalent weight percentages of: 30 to 60% $B_2O_3$; 0.5 to 20% $ZrO_2$; 3 to 30% $Na_2O$; 0.1 to 15% $K_2O$; 5 to 30% CaO; and 1 to 5% $P_2O_5$ in weight percents based on 100 wt % of the total composition.

In embodiments, the abovementioned bioactive borate glass composition is free of MgO.

In embodiments, the abovementioned bioactive borate glass composition is free of $Al_2O_3$, free of $SiO_2$, free of MgO, or free of mixtures thereof.

In embodiments, the abovementioned bioactive borate glass composition can further comprise a source of fluoride ion selected from sodium fluoride (NaF), stannous fluoride ($SnF_2$), calcium fluoride ($CaF_2$), and like fluoride ion sources, or mixtures thereof.

In embodiments, the disclosure provides a method of treating dentin hypersensitivity comprising: contacting at least one surface of a tooth sample having at least one indication of dentin hypersensitivity with a formulation including any of the disclosed compositions.

In embodiments, the contacting can be accomplished, for example, at time zero on at least one Day 1.

In embodiments, the contacting can be accomplished, for example, from 1 to 10 times daily for a period of from 1 to 12 weeks.

The present disclosure is advantaged in several aspects, including for example:

the disclosed $ZrO_2$ containing borate glass compositions was unexpectedly found to have excellent biocompatibility; and the disclosed $ZrO_2$ containing borate glass compositions had unexpectedly faster dentin tubule plugging rates compared to known silicate glass compositions.

Referring to the Figures, FIGS. 1A to 1F show optical images of cell morphology from live/dead cells assay over a seven (7) day period. Cell culture was accomplished on glass discs (12.5 mm in diameter×2.0 mm thick) of Composition 1 in 24-well culture plates. In original color images (not provided), green image spots (portrayed by solid dots) represent the viable cells, and red spots (portrayed by open dots) represent dead cells. Comparison composition (i.e., Control 1 (45S5)) (FIGS. 1A to 1C) and Example Composition 1 (FIGS. 1D to 1F) were used for the cell morphology study.

FIG. 2 shows an ATP assay for Example Composition 1. An ATP assay was used to determine cell proliferation and cytotoxicity in mammalian cells for the disclosed compositions. Cell culture was accomplished on a glass disc (12.5 mm in diameter×2.0 mm thick) for Composition 1, in 24-well culture plate. The higher the readout luminescence (measured at the end of Day 1, Day 4, and Day 7), the larger the cell number.

FIGS. 3A to 3D show SEM micrographs of the test dentin discs having different treatments: a control dentin disc without any treatment (untreated; 3A); a dentin disc treated with a toothpaste base formulation (i.e., carrier only) for one week (3B); a dentin disc treated with 45S5 (Comparison Control 1) containing toothpaste for one week (3C); and a dentin disc treated with a disclosed toothpaste containing Example Composition 1 for one week (3D). All samples were immersed in artificial saliva during the treatment. There was no occluding of dentin tubules for the toothpaste base formulation (3B). After treatment with the 45 S5 containing toothpaste, half the dentin tubules were occluded by crystal-like deposits (3C). After treatment with the Example Composition 1 containing toothpaste, all dentin tubules and dentin surfaces were occluded by crystal-like deposits (3D).

Table 1 lists exemplary $ZrO_2$ containing borate glass compositions and Control compositions 1 and 2.

TABLE 1

$ZrO_2$ containing borate glass compositions and Controls.

| Oxides (mol %) | Comp. 1 | Comp. 2 | Example 1 | Example 2 | Example 3 | Example 4 |
|---|---|---|---|---|---|---|
| $SiO_2$ | 46.5 | 0 | 0 | 0 | 0 | 0 |
| $B_2O_3$ | 0 | 54.4 | 52.5 | 50.6 | 48.8 | 47.1 |
| $P_2O_5$ | 2.6 | 1.8 | 1.6 | 1.6 | 1.5 | 1.5 |
| $Na_2O$ | 24.2 | 6.0 | 5.8 | 5.6 | 5.4 | 5.2 |
| $K_2O$ | 0 | 7.9 | 7.6 | 7.3 | 7.1 | 6.8 |
| MgO | 0 | 7.7 | 7.4 | 7.1 | 6.9 | 6.6 |
| CaO | 26.8 | 22.2 | 21.3 | 20.5 | 19.7 | 19.1 |
| $ZrO_2$ | 0 | 0 | 3.8 | 7.4 | 10.7 | 13.8 |

Each dental formulation was evaluated for the ability to occlude dentine discs made of human molars as specified in Table 2.

TABLE 2

Base and an exemplary bioactive glass containing toothpaste composition.

| Ingredients (in wt %) | Base (control) | Toothpaste (base + BG*) |
|---|---|---|
| glycerol | 69.02 | 64.02 |
| sodium lauryl sulfate | 1.1 | 1.1 |
| PEG400 | 20 | 20 |
| silicon dioxide | 8 | 8 |
| *bioactive glass (BG) | — | 5 |
| Carbopol 940 | 0.5 | 0.5 |
| sodium saccharin | 0.35 | 0.35 |
| flavor | 1.03 | 1.03 |
| Total | 100 | 100 |

Raw materials, equipment, or both, used to produce the glass composition of the present invention, can introduce certain impurities or components that are not intentionally added, and can be present in the final glass composition. Such materials can be present in the glass composition in minor amounts and are referred to herein as "tramp materials."

Disclosed glass compositions can comprise the tramp materials, typically in trace amounts. Similarly, "iron-free," "sodium-free," "lithium-free," "zirconium-free," "alkali earth metal-free," "heavy metal-free," or like characterizations, mean that the tramp material was not purposefully added to the composition, but the composition may still comprise iron, sodium, lithium, zirconium, alkali earth metals, or heavy metals, etc., but in approximately tramp or trace amounts.

Unless otherwise specified, the concentrations of all constituents recited herein are expressed in terms of weight percent (wt %).

While various features, elements or steps of particular embodiments can be described using the transitional phrase "comprising," in alternative embodiments, including those that may be described using the transitional phrases "consisting" or "consisting essentially of," are possible.

EXAMPLES

The following Examples demonstrate making, use, and analysis of the disclosed compositions, formulations, and methods in accordance with the above general procedures.

Example 1

Glass Preparation

The composition of Example 1 in Table 1 was prepared as follows: The source batch materials in the indicated amounts, including boric acid, sodium carbonate, potassium carbonate, limestone, magnesium oxide, calcium phosphate, and zircon were combined. The batch source materials were vigorously mixed in a plastic jar using a Turbular mixer. Then the mixture was transferred to a platinum crucible with an internal volume of approximately 650 cc. The crucible was then loaded into an annealing furnace to calcine the batch at 250° C. for 24 hr. The calcined batch was then melted at 1100 to 1300° C. for 6 hr and then the glass melt was poured on a steel plate, and annealed at 400 to 500° C.

Example 2

Dental Formulation

The dental formulations of Table 2 were each prepared, for example, as follows: glycerol and PEG 400 were first added to the glass composition of Example 1 in Table 1 having a particle size of from 1 to 10 microns produced by jet milling, then the remaining ingredients of the formulation were added and thoroughly mixed with a spatula.

Example 3

Evaluation of Dental Formulation

The dental formulations as mentioned in Example 2 were evaluated as follows: Human molars were lawfully obtained from bforbones (bforbones.com). Dentine discs having a thickness of 1 mm were cut perpendicularly to the long axis of the tooth above the cemento-enamel junction using a Buehler low-speed water cooled diamond saw. A smear layer was created on both sides of the dentine discs by sanding 30 seconds using 500-grit sanding paper. The smear was subsequently removed by treating with 6% citric acid for 3 mins, then rinsed with water, and dried at 37° C. The dentine discs were randomly divided into control or experiment groups, each containing at least three sample specimens, which received either a non-aqueous toothpaste base formulation (blank) or a toothpaste containing 5% of 45S5 (Control composition 1); and the toothpaste containing a disclosed glass composition, as listed in Table 1 and Table 2. The toothpaste and a powered tooth brush were used to brush against both sides of the dentin discs for 1 min per side. The specimens were then rinsed with distilled water to remove visible traces of toothpaste, and then stored in artificial saliva (1.5 mM $CaCl_2$, 0.9 mM $KH_2PO_4$, 130 mM KCl, and 20 mM HEPES with pH 7.4). The procedure of brushing, rinsing, and storing each specimen in artificial saliva was repeated twice a day for 7 days, then the specimens were dried at 37° C. for 16 hrs and stored at RT before SEM.

The disclosure has been described with reference to various specific embodiments and techniques. However, it should be understood that many variations and modifications are possible while remaining within the scope of the disclosure.

What is claimed is:

1. A bioactive borate glass composition comprising:
   30 to 60% $B_2O_3$;
   0.5 to 20% $ZrO_2$;
   3 to 30% $Na_2O$;
   0.1 to 15% $K_2O$;
   0.1 to 15% MgO;
   5 to 30% CaO; and
   1 to 5% $P_2O_5$ in mol percents based on 100 mol % of the total composition.

2. The bioactive borate glass composition of claim 1 wherein the composition is free of $Al_2O_3$, $SiO_2$, or mixtures thereof.

3. The bioactive borate glass composition of claim 1 further comprising a source of fluoride ion selected from NaF, $SnF_2$, $CaF_2$, or mixtures thereof, in an amount of from 1 to 25 mol % by super addition to the composition.

4. A method of treating dentin hypersensitivity comprising:
 contacting at least one surface of a tooth sample having at least one indication of dentin hypersensitivity with a formulation including the composition of claim 1.

5. The method of claim 4 wherein the contacting is accomplished at time zero on at least one Day 1.

6. The method of claim 4 wherein the contacting is accomplished from 1 to 10 times daily for a period of from 1 to 12 weeks.

\* \* \* \* \*

UNITED STATES PATENT AND TRADEMARK OFFICE
CERTIFICATE OF CORRECTION

PATENT NO. : 11,198,638 B2
APPLICATION NO. : 16/202873
DATED : December 14, 2021
INVENTOR(S) : Huayun Deng et al.

Page 1 of 2

It is certified that error appears in the above-identified patent and that said Letters Patent is hereby corrected as shown below:

On the Title Page

In Column 1, item (72), Inventors, Line 2, delete "Pianted" and insert -- Painted --.

In Column 1, item (72), Inventors, Line 3, delete "Pianted" and insert -- Painted --.

On page 2, in Column 2, item (56), Other Publications, Line 13, delete "Si02—Na20" and insert -- SiO2—Na2O --.

On page 2, in Column 2, item (56), Other Publications, Line 13, delete "≤" and insert -- — --.

On page 2, in Column 2, item (56), Other Publications, Lines 13-14, delete "03—Ca0—P205_B203" and insert -- O3—CaO—P2O5_B2O3 --.

On page 3, in Column 1, item (56), Other Publications, Line 38, delete "SiO2Na" and insert -- SiO2.Na --.

On page 3, in Column 1, item (56), Other Publications, Line 38, delete "0.CaO" and insert -- O.CaO --.

On page 3, in Column 1, item (56), Other Publications, Line 41, delete "Fires" and insert -- Pires --.

On page 3, in Column 2, item (56), Other Publications, Line 13, delete "Microplasitcs" and insert -- Microplastics --.

On page 3, in Column 2, item (56), Other Publications, Line 14, delete "2009))." and insert -- 2009). --.

On page 4, in Column 1, item (56), Other Publications, Line 7, delete "Monoflurophosphate" and insert -- Monofluorophosphate --.

Signed and Sealed this
Fourth Day of October, 2022

Katherine Kelly Vidal
*Director of the United States Patent and Trademark Office*

CERTIFICATE OF CORRECTION (continued)
U.S. Pat. No. 11,198,638 B2

On page 4, in Column 1, item (56), Other Publications, Line 18, delete "Propmotes" and insert -- Promotes --.

On page 4, in Column 1, item (56), Other Publications, Line 28, delete "Properites" and insert -- Properties --.

On page 4, in Column 1, item (56), Other Publications, Line 41, delete "Additiona" and insert -- Addition --.

On page 4, in Column 1, item (56), Other Publications, Line 43, delete "Internaitonal;" and insert -- International; --.

On page 4, in Column 2, item (56), Other Publications, Line 5, delete "ArticleI D" and insert -- ArticleID --.

On page 4, in Column 2, item (56), Other Publications, Line 8, delete "Meech" and insert -- Mech. --.

On page 4, in Column 2, item (56), Other Publications, Line 11, delete "Dellvery"," and insert -- Delivery", --.

On page 4, in Column 2, item (56), Other Publications, Line 13, delete "stronium" and insert -- strontium --.

On page 4, in Column 2, item (56), Other Publications, Line 22, delete "aspromising" and insert -- as promising --.

On page 4, in Column 2, item (56), Other Publications, Line 43, delete "B2O3—SiO2—P2O5—Na2O—CaO" and insert -- $B_2O_3$—$SiO_2$—$P_2O_5$—$Na_2O$—CaO --.

On page 4, in Column 2, item (56), Other Publications, Line 45, delete "Osteoblatsic" and insert -- Osteoblastic --.

On page 4, in Column 2, item (56), Other Publications, Lines 46-47, delete "SiO2.Na2O.CaO.K 2O.Mg O.P2O5" and insert -- $SiO_2.Na_2O.CaO.K_2O.MgO.P_2O_5$ --.

On page 4, in Column 2, item (56), Other Publications, Line 47, delete "Al2O3 and B2O3" and insert -- $Al_2O_3$ and $B_2O_3$ --.